US011918235B1

(12) United States Patent
Streit et al.

(10) Patent No.: US 11,918,235 B1
(45) Date of Patent: Mar. 5, 2024

(54) TISSUE PROTECTION SLEEVE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Oliver Streit, Tuttlingen (DE); Nathaniel Kelley Grusin, Germantown, TN (US); Henry B. Faber, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 222 days.

(21) Appl. No.: 17/465,919

(22) Filed: Sep. 3, 2021

Related U.S. Application Data

(60) Provisional application No. 63/074,037, filed on Sep. 3, 2020.

(51) Int. Cl.
*A61B 17/17* (2006.01)
*A61B 17/16* (2006.01)

(52) U.S. Cl.
CPC ...... *A61B 17/1717* (2013.01); *A61B 17/1633* (2013.01); *A61B 17/164* (2013.01)

(58) Field of Classification Search
CPC ... A61B 17/1633; A61B 17/164; A61B 17/17; A61B 17/1703; A61B 17/1717; A61B 17/1721
See application file for complete search history.

(56) References Cited

U.S. PATENT DOCUMENTS 6,419,678 B1 * 7/2002 Asfora ............... A61B 17/1757
606/96
6,656,189 B1 * 12/2003 Wilson ................... A61B 90/92
606/97

(Continued)

OTHER PUBLICATIONS

Author Unknown—Globus Medical AUTOBAHN(tm) Tibial Nailing System, Surgical Technique Guide, www.globusmedical.com/trauma, Dec. 2018.

(Continued)

*Primary Examiner* — Eric S Gibson
(74) *Attorney, Agent, or Firm* — KDW Firm PLLC

(57) ABSTRACT

A tissue protection sleeve for use in trauma surgery is disclosed. In various embodiments, the tissue protection sleeve includes an inner sleeve with a first end portion, a second end portion, a longitudinal axis, and a bore extending there through, and an outer sleeve at least partially surrounding and coupled to the inner sleeve, wherein the tissue protection sleeve is capable of flexing or bending without collapsing the bore. In some embodiments, the inner sleeve may include a number of distinct geometries to provide sufficient structural rigidity, whilst still allowing the inner sleeve to bend. Additionally, a tissue protection sleeve handle may be coupled to the tissue protection sleeve to allow for manipulation of the tissue protection sleeve. In certain embodiments, pin guide holes or channels may be used to secure the tissue protection sleeve to a patient's bone.

11 Claims, 18 Drawing Sheets

(56) References Cited

U.S. PATENT DOCUMENTS

| | | | |
|---|---|---|---|
| 7,422,594 B2* | 9/2008 | Zander | A61B 17/17 606/103 |
| 9,101,432 B2* | 8/2015 | Limouze | A61B 17/164 |
| 9,566,078 B2* | 2/2017 | Hirsch | A61B 17/1764 |
| 9,999,430 B2* | 6/2018 | Hirsch | A61B 17/3431 |
| 10,117,699 B2* | 11/2018 | Limouze | A61B 17/1717 |
| 11,490,942 B2* | 11/2022 | El Zoghbi | A61B 17/1764 |
| 2005/0119663 A1* | 6/2005 | Keyer | A61B 17/17 606/96 |
| 2013/0023891 A1* | 1/2013 | Berberich | A61B 17/1764 606/98 |
| 2013/0172890 A1* | 7/2013 | Limouze | A61B 17/1675 606/62 |
| 2013/0178860 A1* | 7/2013 | Dorawa | A61B 17/17 606/96 |
| 2013/0190570 A1* | 7/2013 | Hirsch | A61B 17/00234 600/204 |
| 2013/0310886 A1* | 11/2013 | VanOsten | A61B 17/1717 606/329 |
| 2014/0039264 A1* | 2/2014 | Heiman | A61B 5/24 600/210 |

OTHER PUBLICATIONS

Author Unknown—DePuy Synthes Suprapatellar Instrumentation for Titanium Cannulated Tibial Nails, Surgical Technique, 2013-2017.

Author Unknown—Stryker T2 Alpha (tm) Tibia Nailing System, Operative technique, www.stryker.com, (2019).

* cited by examiner

TISSUE PROTECTION SLEEVE

CROSS-REFERENCE TO RELATED APPLICATIONS

This is a non-provisional of, and claims the benefit of the filing date of, pending U.S. provisional patent application No. 63/074,037, filed Sep. 3, 2020, entitled "Tissue Protection Sleeve", the entirety of which application is incorporated by reference herein.

FIELD OF THE DISCLOSURE

The present disclosure relates generally to orthopedic devices and more particularly to a tissue protection sleeve that may be used to, for example, insert an intramedullary ("IM") nail into a patient's bone. Alternatively, the tissue protection sleeve may be used to guide a reamer for reaming an intramedullary canal of the patient's bone. In one embodiment, the tissue protective sleeve includes a soft, flexible outer material or sleeve positioned over an articulating or otherwise flexible interior tube or sleeve to protect articular anatomical surfaces and other tissues during IM nail insertion, while maintaining a consistent opening for insertion of the IM nail.

BACKGROUND OF THE DISCLOSURE

Tissue protection sleeves or other protective structures have been used to provide protected pathways during, for example, implanting or inserting intramedullary ("IM") nails, especially at a proximal tibial where a patient's patellar structures and other soft tissues need to be protected. Rubber sleeves or other flexible structures are useful in providing additional protection for the patient's patellar structures and other soft tissues. Rubber sleeves or other flexible structures are however subjected to collapse without adequate reinforcement (e.g., decreasing in size or cross-sectional area of the pathway or bore through the rubber sleeve or structure).

Thus, a challenge with using rubber sleeves during the implanting of an IM nail is to provide an adequate structure to maintain a pathway while allowing for the insertion of IM nails that have a curvature. In other words, a narrow, open structure is desirable to minimize tissue displacement and trauma, but if the structure is too narrow, an IM nail with a curved section will not pass through the opening and a next-larger-size tube or sleeve may be required.

Thus, it would be advantageous to provide an improved tissue protection sleeve such as, for example, one including a flexible outer sleeve in combination with an inner sleeve that is arranged and configured to flex, bend, or articulate while maintaining an uncollapsed (e.g., non-collapsed) or consistent opening, bore, or pathway in the form of a curved pathway through soft tissue to enable, for example, insertion of an IM nail.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure illustrates and describes various embodiments of a tissue protection sleeve comprising an inner sleeve with a first end portion, a second end portion, a longitudinal axis and an opening, bore, or pathway (terms used interchangeably herein without the intent to distinguish) extending there through, and an outer sleeve at least partially surrounding and coupled to the inner sleeve, wherein the tissue protection sleeve is arranged and configured to flex or bend without collapsing, in part or in total, the bore so that a consistent pathway or opening is formed therein.

In some embodiments, the outer sleeve may be molded over the inner sleeve. In addition, and/or alternatively, the outer sleeve may cover all surfaces of the inner sleeve, or may cover only portions of the inner sleeve. In addition, and/or alternatively, the outer sleeve may be a polymer. For example, the polymer may comprise silicone rubber.

In some embodiments, the bore of the tissue protection sleeve may decrease or increase in cross-sectional area from the first end portion to the second end portion. The bore may be cylindrical or oval in cross-section. Alternatively, the bore may be a variety of cross sections that change from the first end portion to the second end portion.

In some embodiments, the inner sleeve may comprise a metal, a plastic, a polymer, a fiber reinforced polymer, or combinations thereof, or any other material capable of resisting collapse to maintain an uncollapsed opening through the tissue protection sleeve. In some embodiments, the tissue protection sleeve may be intended for one-time use only or it may be reused.

In some embodiments, the inner sleeve may comprise a plurality of discrete, separated segments, although in some embodiments, the segments may be coupled to each other. In some embodiments, the plurality of segments may interdigitate as the tissue protection sleeve is flexed to facilitate bending of the tissue protection sleeve along a preferred axis. In addition, and/or alternatively, the inner sleeve may comprise a plurality of frustoconical shapes arranged along the longitudinal axis from the first end portion to the second end portion.

In other embodiments, at least a portion of the inner sleeve may comprise a unitary or integral member, sleeve, or tube (terms used interchangeably herein without the intent to distinguish) including one or more cuts. The one or more cut are arranged and configured to allow bending of the tissue protection sleeve. In one embodiment, the one or more cuts may be arranged in a spiral pattern. In yet other embodiments, the one or more cuts may comprise an interrupted spiral cut pattern, a bespoke cut pattern, or a radial cut pattern.

In addition, the tissue protection sleeve may include one or more pin guides, openings, or channels (terms used interchangeably herein without the intent to distinguish) to allow passage of one or more bone pins to fix or couple the tissue protection sleeve to a patient's bone. In some embodiments, the pin guides may share a common opening with the bore of the tissue protection sleeve (e.g., the pin channels include an opening, the opening being in communication with the bore formed in the tissue protection sleeve so that a pin can be moved between the bore and the opening). Alternatively, in some embodiments, the pin guides may be positioned on the outside of the tissue protection sleeve.

In addition, and/or alternatively, the tissue protection sleeve may include one or more pin holes adjacent to the first end portion. The pin holes may extend in a generally transverse direction relative to the longitudinal axis of the tissue protection sleeve. In use, the pin holes are arranged and configured to receive one or more bone pins to fix or couple the tissue protection sleeve to a patient's bone.

In addition, and/or alternatively, the tissue protection sleeve may include a handle coupled thereto. For example, in one embodiment, the tissue protection sleeve may include a transverse opening positioned adjacent to the first end portion of the tissue protection sleeve. In use, the handle is arranged and configured to engage the tissue protection sleeve via the transverse opening.

In additional embodiments, the tissue protection sleeve may include an outer sleeve and a pin sleeve. In use, the outer sleeve may be arranged and configured to at least partially surround and couple to the pin sleeve. In use, the pin sleeve may be provided with one or more peripheral pin channels (e.g., pin locator holes) and a central pin channel. In use, the central pin channel may be arranged and configured to position a pin, which may then be used to guide an intramedullary reamer. The periphery pin channels may be arranged and configured to receive one or more pins, respectively, for fixing or coupling the tissue protection sleeve to a patient's bone.

In further embodiments, a tissue protection kit is provided for use in a surgery. The kit may include at least one of an inner sleeve, an outer sleeve, and a pin sleeve. The kit may be provided in a sterile package. In certain embodiments, the tissue protection kit may comprise an inner sleeve and an outer sleeve, only an outer sleeve and a non-disposable inner sleeve, or a pin sleeve and an outer sleeve.

Embodiments of the present disclosure provide numerous advantages. In one non-limiting example advantage, the embodiments provide both flexibility and opening maintenance in a potentially smaller form factor than the prior art. In some embodiments, the designs are the same shape as one or both of the prior art rigid inner outer sleeves and flexible outer sleeves and may therefore be used with existing instrumentation. Especially where the construct is a plastic/silicone combination, the tissue protection sleeves may be a disposable item and provides the surgeon with a new part free from burrs or nicks commonly caused by re-use and therefore protects articular cartilage from damage during the sleeve's insertion. An additional benefit of the tissue protection sleeve being disposable is enhanced sterility control and higher profitability. Another advantage of the current disclosure is that the tissue protection sleeve can offer the benefits described above while taking up less space within the soft tissues.

Still yet another advantage of the current disclosure is that either or both of a set of pins may be used to stabilize the tissue protection sleeve. Particularly, the tissue protection sleeve may be pinned to either or both of a patient's tibia and femur. Yet another advantage of the current disclosure is that once the tissue protection sleeve is pinned to a bone, it does not need to be pulled on by the weight of the sleeve handle. The fixation pin holes of the various embodiments of the tissue protection sleeve do not go through corresponding holes in the heavier entry tube handle. This allows the surgeon the option of detaching the tissue protection sleeve handle from the tissue protection sleeve if they need to during the procedure, i.e., during insertion of the nail.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
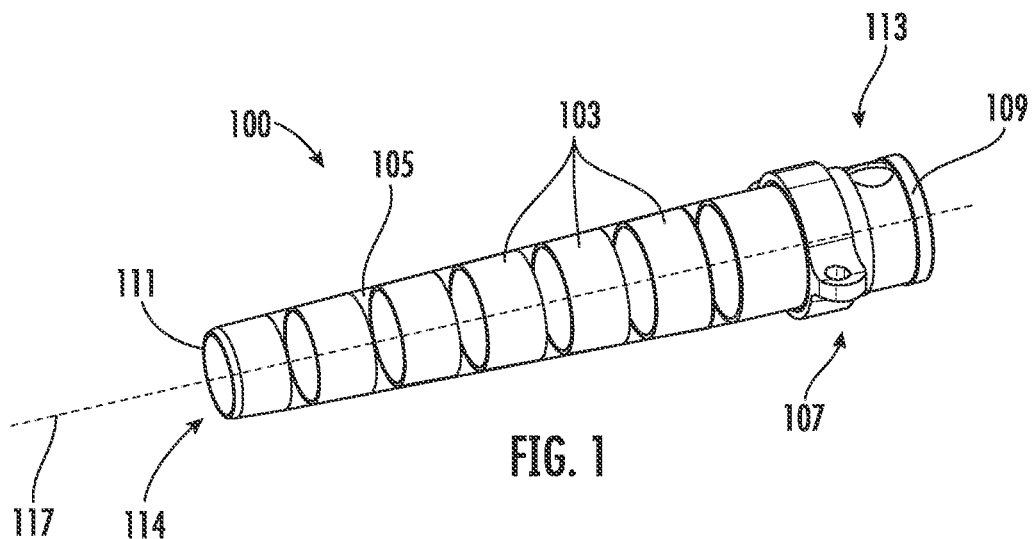
FIG. 1 illustrates a perspective view of an embodiment of a tissue protection sleeve in accordance with one or more features of the present disclosure.

The drawings are not necessarily to scale. The drawings are merely representations, not intended to portray specific parameters of the disclosure. The drawings are intended to depict various embodiments of the disclosure, and therefore are not be considered as limiting in scope. In the drawings, like numbering represents like elements.

DETAILED DESCRIPTION

Various features or the like of a tissue protection sleeve will now be described more fully herein with reference to the accompanying drawings, in which one or more features of the tissue protection sleeve will be shown and described. It should be appreciated that the various features may be used independently of, or in combination, with each other. It will be appreciated that a tissue protection sleeve as disclosed herein may be embodied in many different forms and may selectively include one or more features described herein. As such, the tissue protection sleeve should not be construed as being limited to the specific embodiments set forth herein. Rather, these embodiments are provided so that this disclosure will convey certain features of the tissue protection sleeve to those skilled in the art.

As will be described in greater detail herein, in accordance with one or more features of the present disclosure, the tissue protection sleeve may include a soft, flexible outer material or sleeve positioned over an articulating or otherwise flexible interior tube or sleeve. In use, the tissue protection sleeve is arranged and configured to protect surrounding anatomical surfaces and other tissues of the patient during, for example, insertion of an IM nail, while maintaining a consistent opening through the tissue protective sleeve during insertion of the IM nail. In some embodiments, the soft, flexible outer material or sleeve may be integrated with the articulating or flexible interior tube or sleeve by, for example, overmolding. In some embodiments, the insertion opening, bore, or pathway maintained by the tissue protection sleeve may be straight or curved to accommodate IM nails with some curvature.

Figure 2:
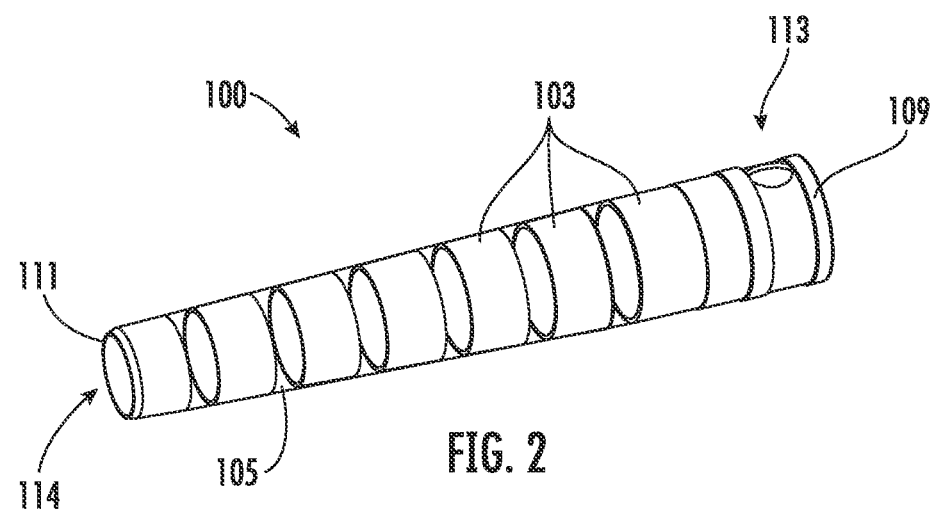
FIG. 2 illustrates an additional perspective view of the tissue protection sleeve shown in FIG. 1.
Figure 3:
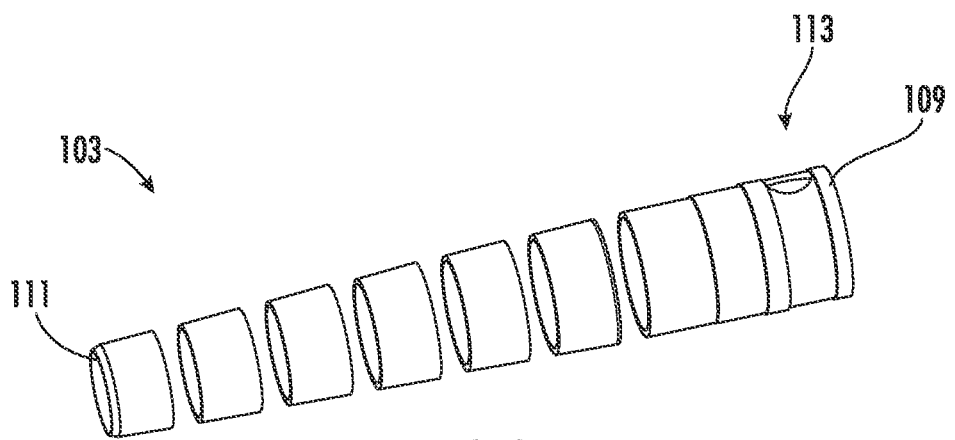
FIG. 3 illustrates an additional perspective view of the tissue protection sleeve shown in FIG. 1, FIG. 3 illustrating components of an inner sleeve.

Referring to the accompanying drawings in which like reference numbers indicate like elements, FIGS. 1-3 illustrate an embodiment of a tissue protection sleeve 100 in accordance with one or more features of the present disclosure. As illustrated, the tissue protection sleeve 100 includes an inner sleeve 103 and an outer sleeve 105. In one embodiment, the inner sleeve 103 includes a plurality of independent and separate segments. That is, the inner sleeve 103 may be formed by a plurality of discrete segments having, for example, a cone or circular shape. Thus arranged, the inner sleeve 103 includes a series of pieces or segments that are designed to be placed near, but not in direct contact to adjacent pieces or segments. In use, the inner sleeve 103 is held together by the outer sleeve 105 positioned or molded thereon. Thus arranged, material forming the outer sleeve 105 may be positioned between spaces or gaps between adjacent pieces or segments of the inner sleeve 103.

In one embodiment, the outer sleeve 105 comprises a flexible outer sleeve. In one embodiment, the outer sleeve 105 may be formed of a polymer, silicone rubber, or any other flexible, resilient material. The outer sleeve 105 may be overmolded onto the inner sleeve 103 (e.g., overmolded onto the plurality of segments forming the inner sleeve 103). The outer sleeve 105 may cover all the surfaces of the plurality of segments forming the inner sleeve 103, or may cover only parts of the plurality of segments forming the inner sleeve 103. Thus arranged, the flexible material comprising the outer sleeve 105 may coat the exterior of the inner sleeve 103, as well as the interior and the ends in some embodiments.

In use, the outer sleeve 105 is arranged and configured to flex, bend, articulate, or the like (terms used interchangeably herein without the intent to distinguish) about a longitudinal axis 117 of the tissue protection sleeve 100 and advantageously, allows the tissue protection sleeve 100 to bend without reducing a size or cross-sectional area of an inner bore 114 of the tissue protection sleeve 100. As illustrated, in one embodiment, the inner bore 114 may be provided with a circular cross-sectional shape or area, but other cross sections, such as ovals, are within the scope of this disclosure. Additionally, as illustrated, the inner bore 114 may extend from a first or proximal end portion 109 of the tissue protection sleeve 100 to a second or distal end portion 111 of the tissue protection sleeve 100, the area of the inner bore 114 may vary such as, for example, taper, from the first end portion 109 to the second end portion 111. As such, in some embodiments, the inner bore 114 may be conical or frustoconical.

In use, the tissue protection sleeve 100 may be positioned adjacent to, in contact with, and/or inserted into an end of a patient's long bone such as, for example, a portion of a proximal tibia of the patient. The tissue protection sleeves of the present disclosure are intended to protect soft tissue at the end of the patient's bone (e.g., tibia) during surgery to repair a fracture of the long bone. In the case of a proximal tibia, this may include patellar structures and articulating surfaces of the proximal tibia. In some embodiments, the tissue protection sleeves of the present disclosure may also be coupled with a tissue protection sleeve handle (shown in FIG. 18). In some embodiments, the tissue protection sleeve 100 may include a hole 113 near the first end portion 109. In use, the hole 113 may be used to connect the tissue protection sleeve 100 to the tissue protection sleeve handle, although any other now known or hereafter developed coupling mechanism may be used to couple the tissue protection sleeve 100 to the tissue protection sleeve handle.

Additionally, and/or in the alternative, it is often advantageous to couple or pin the tissue protection sleeve 100 to a patient's bone. As such, in some embodiments, the tissue protection sleeve 100 may include one or more pin holes 107 arranged and configured to receive one or more pins 112 (FIG. 19), respectively, to couple or fix the tissue protection sleeve 100 to the patient's bone, although any other now known or hereafter developed coupling mechanism may be used to couple the tissue protection sleeve 100 to the patient's bone. As illustrated, in one embodiment, the one or more pin holes 107 may be formed in a pin ring arranged and configured to connect to the first or proximal end portion 109 so that pins 112 may be attached through the holes 107 to fix the tissue protection sleeve relative to the anatomy during a procedure.

Figure 4:
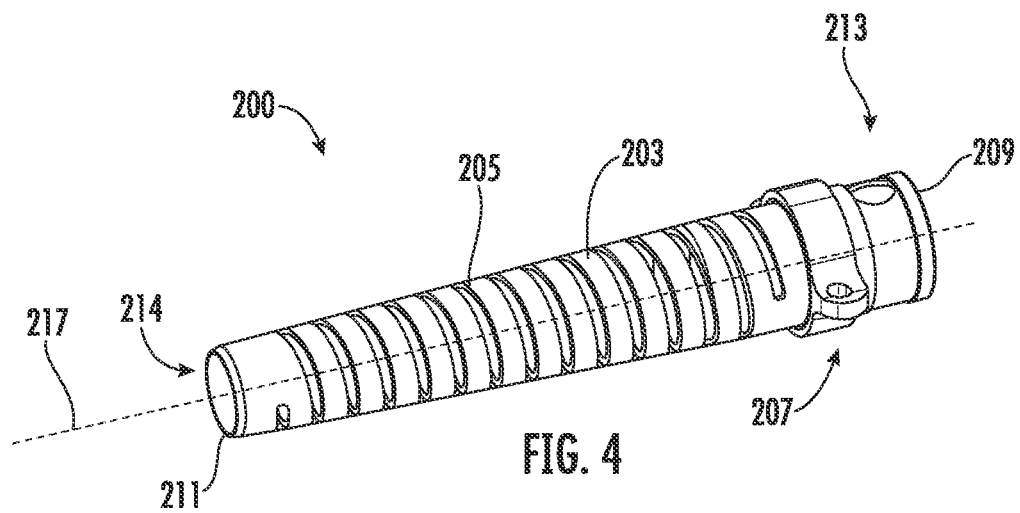
FIG. 4 illustrates a perspective view of a second embodiment of a tissue protection sleeve in accordance with one or more features of the present disclosure.
Figure 5:
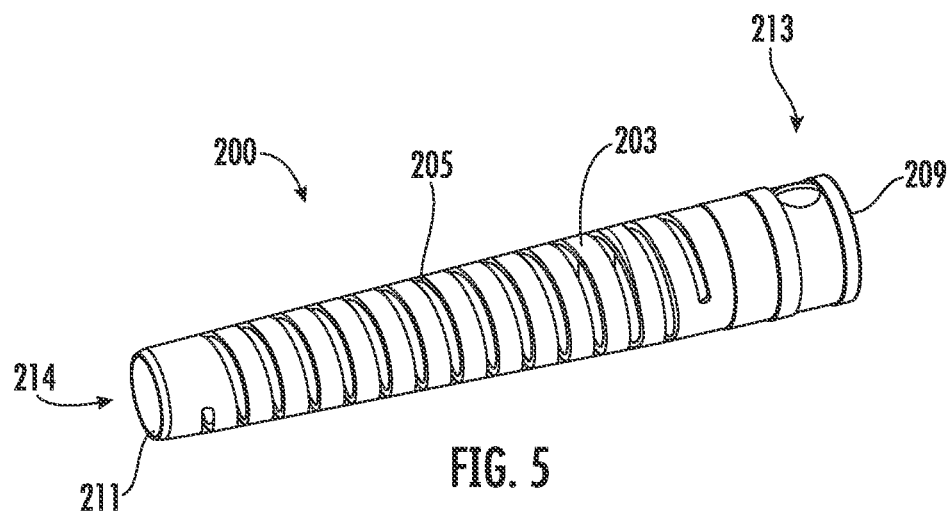
FIG. 5 illustrates an additional perspective view of the tissue protection sleeve shown in FIG. 4.
Figure 6:
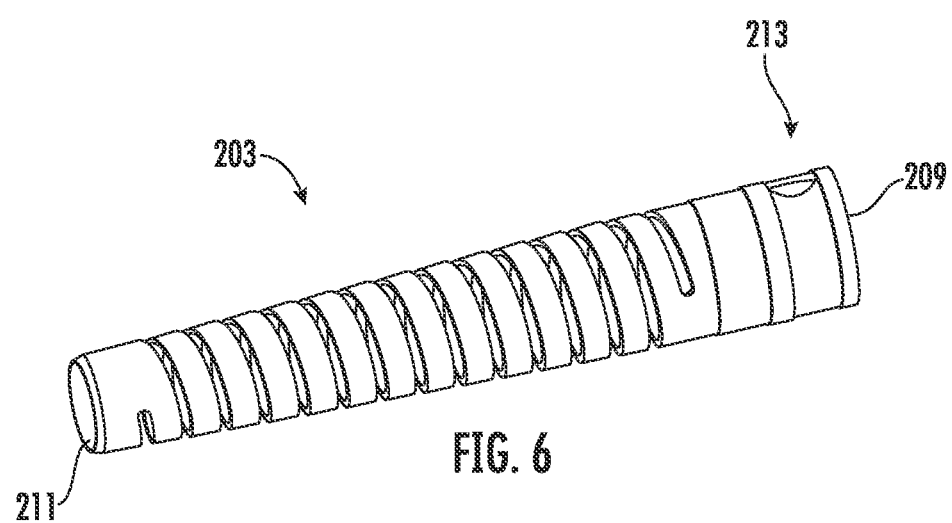
FIG. 6 illustrates an additional perspective view of the tissue protection sleeve shown in FIG. 4, FIG. 6 illustrating components of an inner sleeve.
Figure 7:
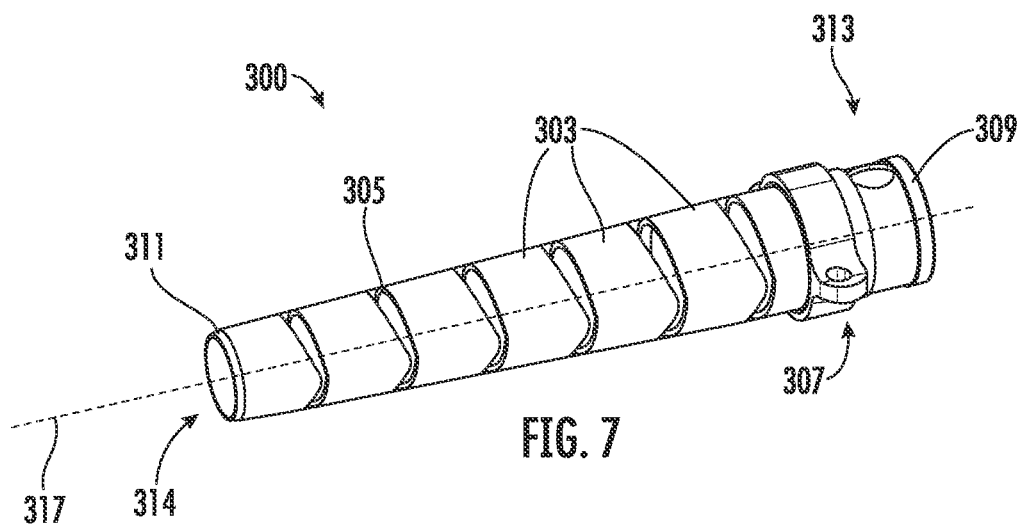
FIG. 7 illustrates a perspective view of a third embodiment of a tissue protection sleeve in accordance with one or more features of the present disclosure.
Figure 8:
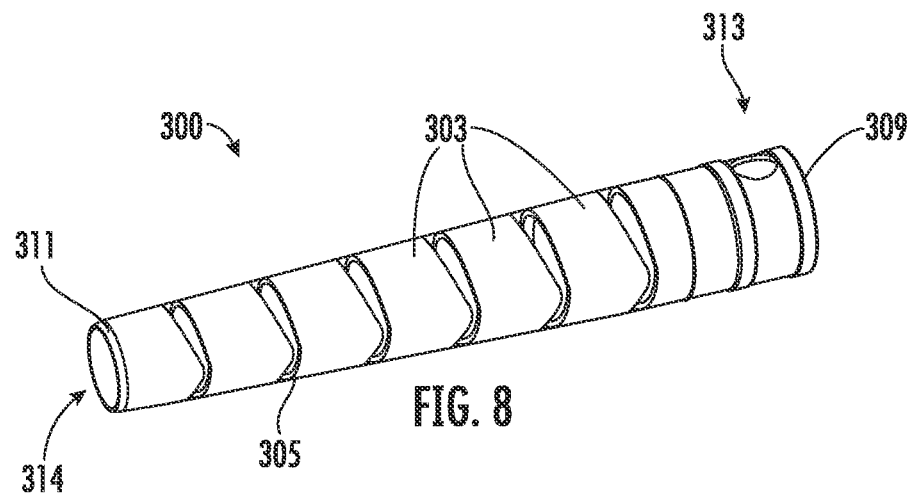
FIG. 8 illustrates an additional perspective view of the tissue protection sleeve shown in FIG. 7.
Figure 9:
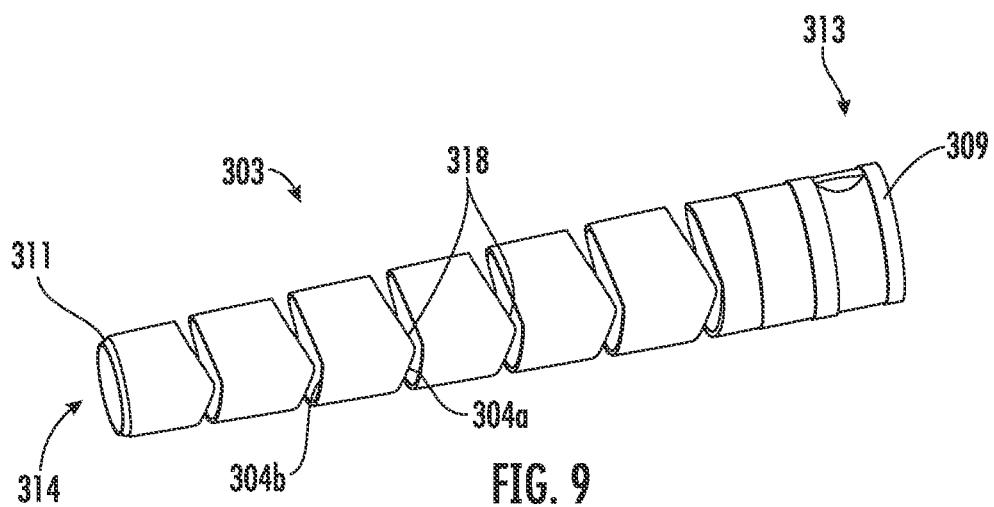
FIG. 9 illustrates an additional perspective view of the tissue protection sleeve shown in FIG. 7, FIG. 9 illustrating components of an inner sleeve.
Figure 10:
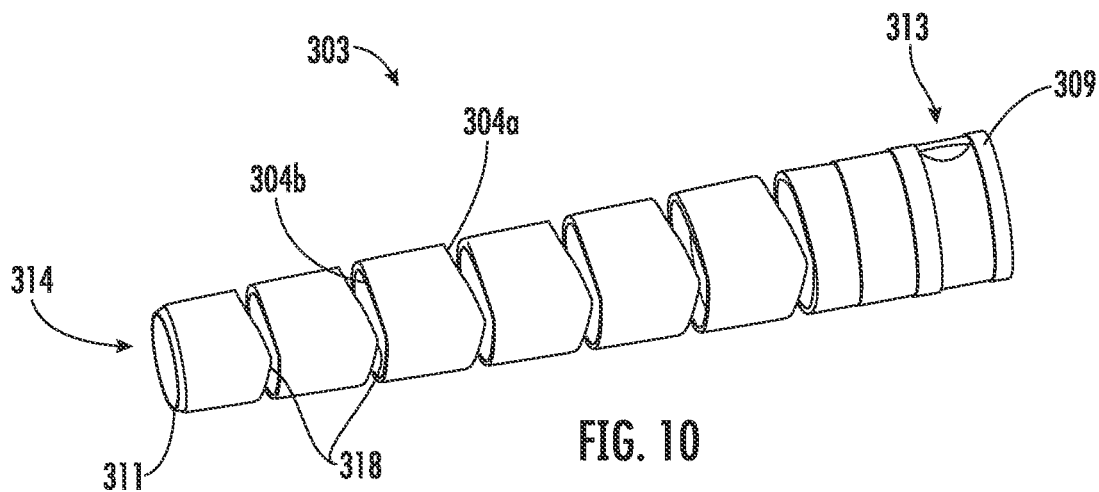
FIG. 10 illustrates an additional perspective view of the tissue protection sleeve shown in FIG. 7, FIG. 10 illustrating components of the inner sleeve.
Figure 11:
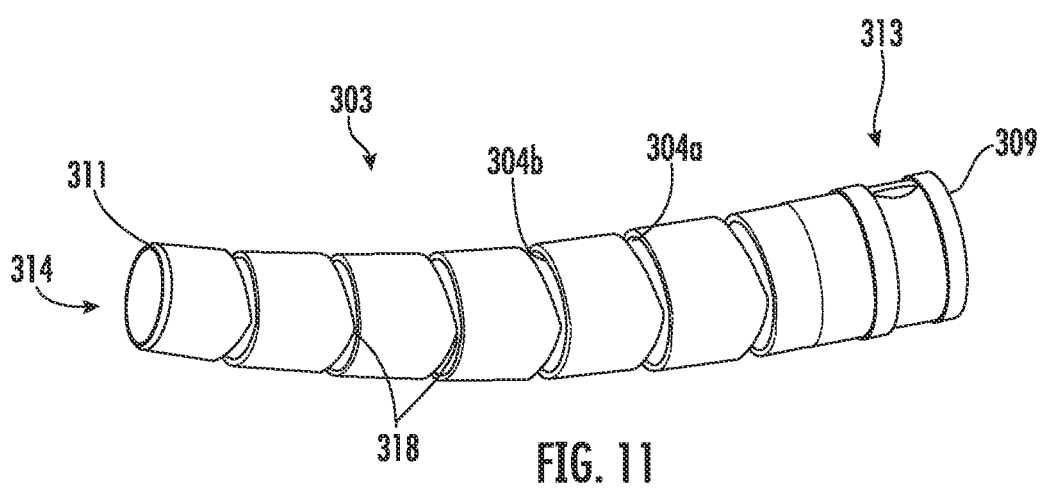
FIG. 11 illustrates an additional perspective view of the tissue protection sleeve shown in FIG. 7, FIG. 11 illustrating the inner sleeve flexing.

Referring to FIGS. 4-6 a second, alternate embodiment of a tissue protection sleeve 200 in accordance with one or more features of the present disclosure is illustrated. In use, tissue protection sleeve 200 is substantially similar to tissue protection sleeve 100 as previously described herein. As such, for the sake of brevity of this disclosure, discussion of some components is omitted herefrom.

Similar to tissue protection sleeve 100 previously described, as illustrated, the tissue protection sleeve 200 includes an inner sleeve 203 and an outer sleeve 205. The outer sleeve 205 may comprise a flexible outer sleeve such as, for example, a polymer overmolded onto the inner sleeve 203. In use, the outer sleeve 205 is arranged and configured to flex or bend about a longitudinal axis 217 of the tissue protection sleeve 200 and advantageously, allows the tissue protection sleeve 200 to bend without reducing the size or cross-sectional area of an inner bore 214 of the tissue protection sleeve 200, which extends from a first or proximal end portion 209 of the tissue protection sleeve 200 to a second or distal end portion 211 of the tissue protection sleeve 200. In addition, as previously mentioned, the tissue protection sleeve 200 may include a hole 213 to connect the tissue protection sleeve 200 to a tissue protection sleeve handle and/or one or more pin holes 207 to receive one or more pins, respectively, to couple or fix the tissue protection sleeve 200 to the patient's bone.

In accordance with tissue protection sleeve 200, the inner sleeve 203 may be formed as a unitary or integral tube. In various embodiments, the inner sleeve 203 is configured to enable flexion or bending thereof. For example, the inner sleeve 203 may include one or more cuts formed therein to facilitate flexing or bending thereof. For example, as illustrated, the inner sleeve 203 may include a cut formed in a spiral configuration (e.g., the inner sleeve 203 is manufactured from a single piece of material with a spiral cut along its length). Thus arranged, in one embodiment, the inner sleeve 203 may be manufactured as a unitary or integral piece. Subsequently, a spiral groove may be cut or formed within the inner sleeve 203 to provide the flexibility.

Referring to FIGS. 7-11 a third, alternate embodiment of a tissue protection sleeve 300 in accordance with one or more features of the present disclosure is illustrated. In use, tissue protection sleeve 300 is substantially similar to tissue protection sleeves 100, 200 as previously described herein. As such, for the sake of brevity of this disclosure, discussion of some components is omitted herefrom.

Similar to tissue protection sleeves 100, 200 previously described, as illustrated, the tissue protection sleeve 300 includes an inner sleeve 303 and an outer sleeve 305. The outer sleeve 305 may comprise a flexible outer sleeve such as, for example, a polymer overmolded onto the inner sleeve 303. In use, the outer sleeve 305 is arranged and configured to flex or bend about a longitudinal axis 317 of the tissue protection sleeve 300 and advantageously, allows the tissue protection sleeve 300 to bend without reducing the size or cross-sectional area of an inner bore 314 of the tissue protection sleeve 300, which extends from a first or proximal end portion 309 of the tissue protection sleeve 300 to a second or distal end portion 311 of the tissue protection sleeve 300. In addition, as previously mentioned, the tissue protection sleeve 300 may include a hole 313 to connect the tissue protection sleeve 300 to a tissue protection sleeve handle and/or one or more pin holes 307 to receive one or more pins, respectively, to couple or fix the tissue protection sleeve 300 to the patient's bone.

In accordance with one or more features of the present disclosure, the tissue protection sleeve 300 includes an inner sleeve 303 arranged and configured as a plurality of independent and separate segments (similar to tissue protection sleeve 100). In use, as illustrated, the inner sleeve 303 may include a proximal side 304a and a distal side 304b. As illustrated, the proximal side 304a includes a curve, a projection, a bump, or the like 318 (terms used interchangeably herein without the intent to distinguish) extending away from the proximal side 304a towards the distal side 304b of an adjacent segment of the inner sleeve 303. Thus arranged, the tissue protection sleeve 300 is arranged and configured to flex or bend less readily in certain directions, as projection 318 will interfere or interdigitate with the next segment in line. This feature may be useful for a surgeon, as tissue structures encountered during surgery may tend to force a tissue protection sleeve to bend. This tissue interference is often encountered by surgeons when inserting a tissue protection sleeve behind a patient's patella. If, however, the bending direction is limited, a surgeon has a better chance of passing a reamer or nail through the tissue protection sleeve and into the entry point or opening formed in the patient's bone.

Figure 12:
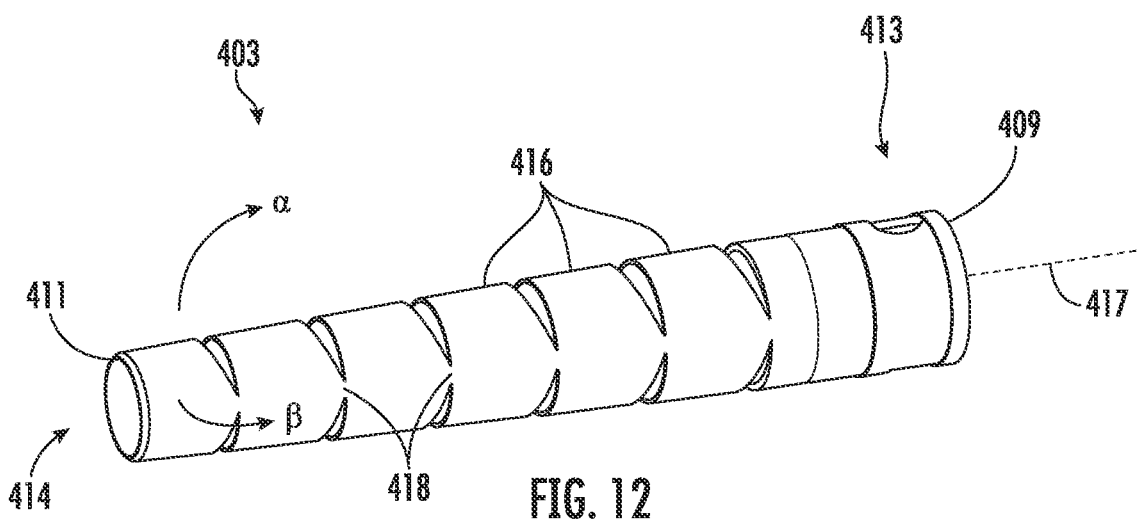
FIG. 12 illustrates a perspective view of a fourth embodiment of a tissue protection sleeve in accordance with one or more features of the present disclosure, FIG. 12 illustrating interdigitation of inner sleeve segments.

Referring to FIG. 12, a fourth embodiment of a tissue protection sleeve in accordance with one or more features of the present disclosure is illustrated. In use, tissue protection sleeve is substantially similar to tissue protection sleeve 300 as previously described herein. As such, for the sake of brevity of this disclosure, discussion of some components is omitted herefrom.

As illustrated and as previously described, the tissue protection sleeve includes an inner sleeve 403 and an outer sleeve (not shown). As previously described, the outer sleeve may comprise a flexible outer sleeve such as, for example, a polymer overmolded onto the inner sleeve 403. In use, the outer sleeve is arranged and configured to flex or bend about a longitudinal axis 417 of the tissue protection sleeve and advantageously, allows the tissue protection sleeve to bend without reducing the size or cross-sectional area of an inner bore 414 of the tissue protection sleeve, which extends from a first or proximal end portion 409 of the tissue protection sleeve to a second or distal end portion 411 of the tissue protection sleeve. In addition, as previously mentioned, the tissue protection sleeve may include a hole 413 to connect the tissue protection sleeve to a tissue protection sleeve handle and/or one or more pin holes to receive one or more pins, respectively, to couple or fix the tissue protection sleeve to the patient's bone.

In accordance with one or more features of the present disclosure, the inner sleeve 403 of the tissue protection sleeve may comprise a plurality of segments 416 that are connected to each other at a curve, a projection, a bump, or the like 418 extending away from a proximal side of the segment towards a distal side of an adjacent segment of the inner sleeve 403. Thus arranged, the inner sleeve 403 is easier to manufacture as compared to inner sleeve 303, as the inner sleeve 403 is not made up of a number of discrete segments, but rather one construct (either unitary or monolithic). This makes the inner sleeve 403 easier to place in a mold if the outer sleeve is to be overmolded around the inner sleeve. Similar to the tissue protection sleeve 300 described in accordance with FIGS. 7-11, the plurality of segments of the inner sleeve 403 also allow the tissue protection sleeve to bend less readily in certain directions. As illustrated, the tissue protection sleeve will move more readily along an arc defined by angle α rather than the arc defined by angle β.

Figure 13:
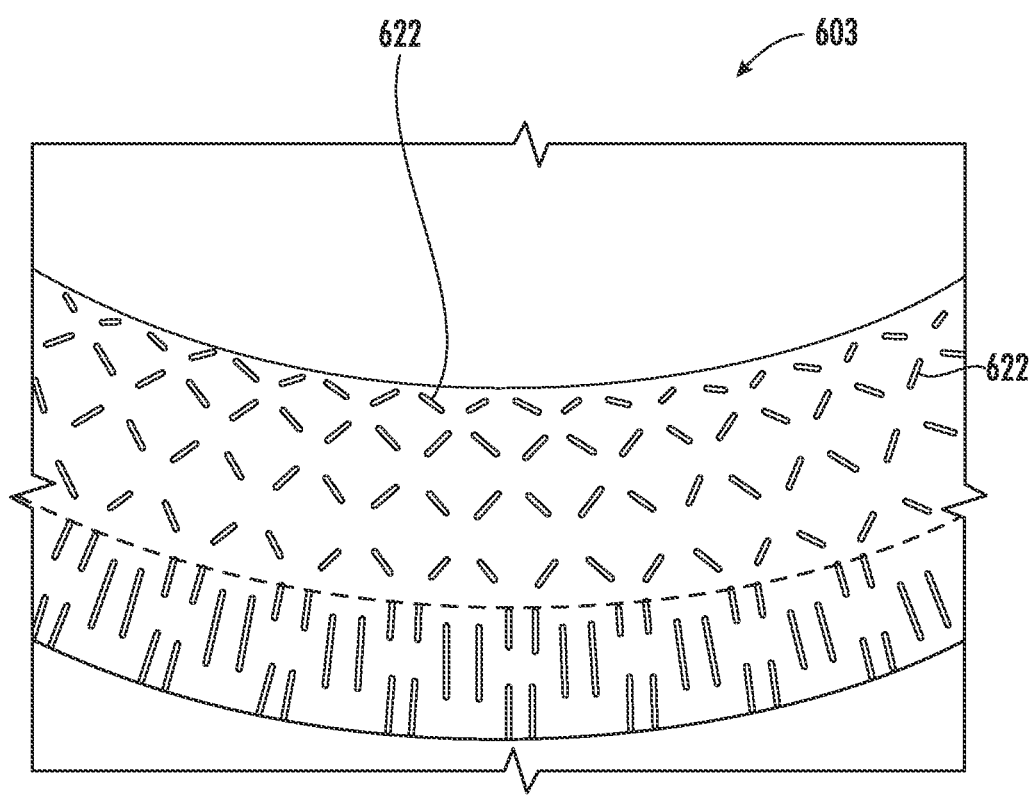
FIG. 13 illustrates a top view of a fifth embodiment of an inner sleeve in accordance with one or more features of the present disclosure, FIG. 13 illustrating an inner sleeve flexing.
Figure 14:
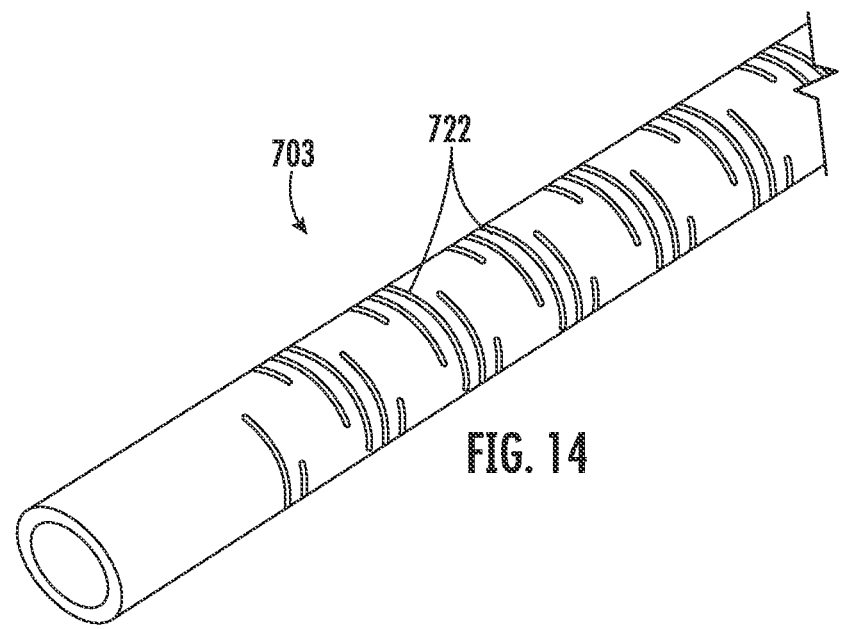
FIG. 14 illustrates a perspective view of a sixth embodiment of an inner sleeve in accordance with one or more features of the present disclosure.
Figure 15:
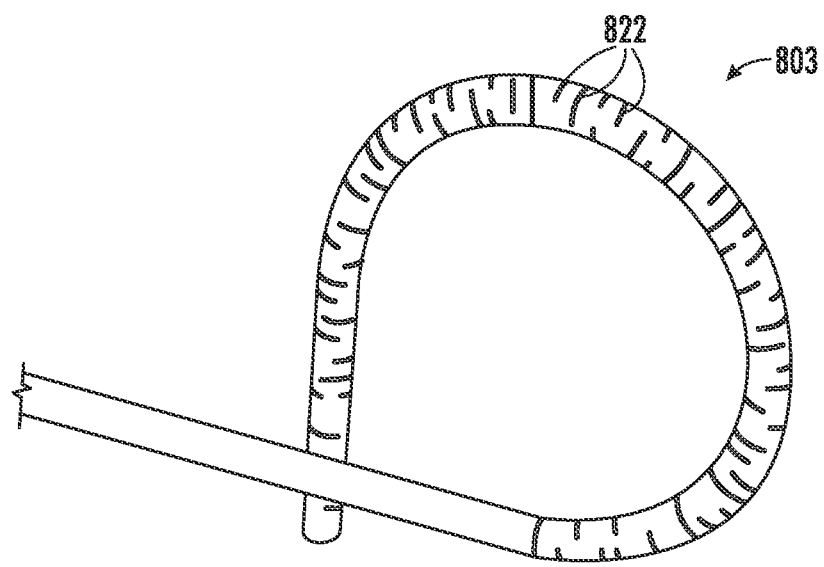
FIG. 15 illustrates a perspective view of a seventh embodiment of an inner sleeve in accordance with one or more features of the present disclosure.

Referring to FIGS. 13-15, a number of alternative designs for an inner sleeve that may be used in a tissue protection sleeve in accordance with one or more features of the present disclosure are illustrated. As previously mentioned, the inner sleeve may be formed as a unitary or integral tube. In various embodiments, as previously mentioned, the inner sleeve is configured to enable flexion or bending thereof. For example, the inner sleeve may include one or more cuts formed therein to facilitate flexing or bending thereof (e.g., the one or more cuts allow the inner sleeve to have greater structural rigidity, yet still be able to bend enough for the purposes of inserting a curved IM nail through the inner bore of the tissue protection sleeve). For example, as previously mentioned in connection with FIGS. 4-6, the inner sleeve 203 may include a cut formed in a spiral configuration (e.g., inner sleeve 203 is formed of a spiral wound ribbon). Alternatively, referring to FIG. 13, the inner sleeve 603 may include a plurality of separate and distinct cutouts 622. As illustrated, each cutout 622 may be formed as a linear segment. As illustrated, the cutouts may resemble, for example, an "X" pattern, however, while each cutout 622 is shown as a linear segment, those of ordinary skill in the art would understand other geometries may be used. Referring to FIG. 14, the inner sleeve 703 may be include a plurality of cutouts 722. As illustrated, the cutouts 722 may be provided as independent and distinct cutouts with each set of cutouts 722 being separated from an adjacent cutout 722 by a distance or space. In use, the cutouts advantageously allow for bending of the inner sleeve 703 whilst maintaining structural rigidity. Referring to FIG. 15, the inner sleeve 803 may include a plurality of cutouts 822 having alternate configurations, which also advantageously allow for bending of the inner sleeve 803 whilst maintaining structural rigidity. As will be appreciated by one of ordinary skill in the art, the inner sleeve may include any shaped cutouts arranged and configured to enable the inner sleeve to flex or bend.

Figure 16:
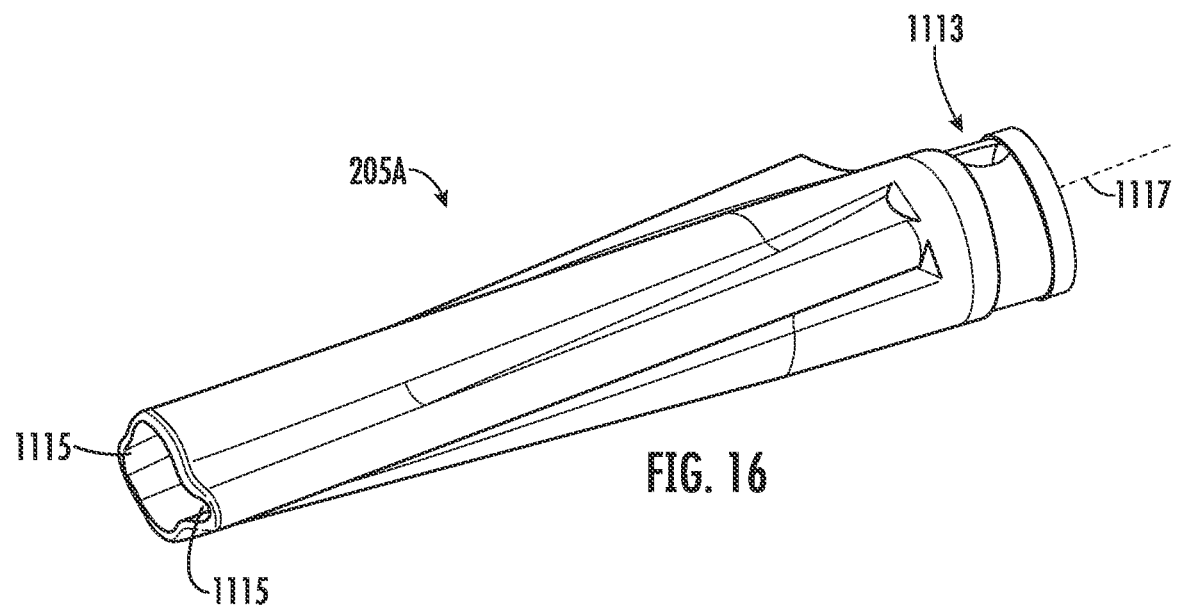
FIG. 16 illustrates a perspective view of a second embodiment of an outer sleeve in accordance with one or more features of the present disclosure, FIG. 16 illustrating integrated pin guides.
Figure 17:
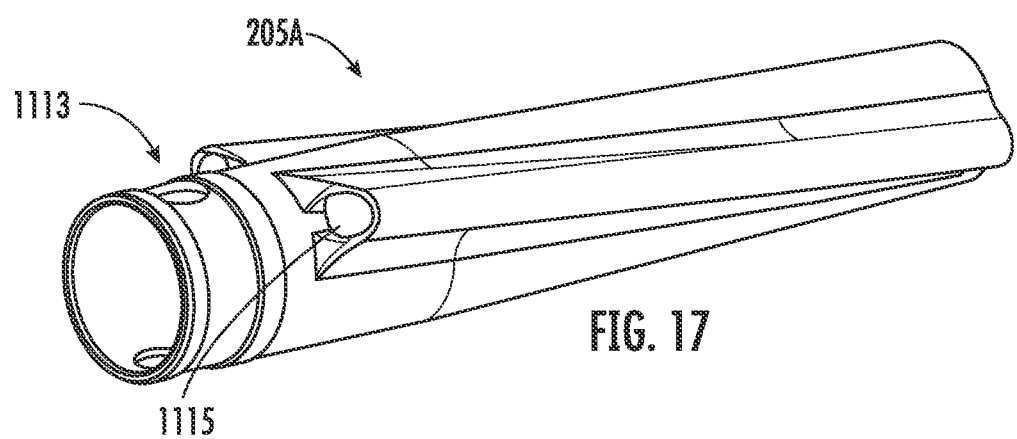
FIG. 17 illustrates an additional perspective view of the outer sleeve shown in FIG. 16.

Referring to FIGS. 16 and 17, a second embodiment of an outer sleeve 205A is illustrated. In use, the outer sleeve 205A may be used in connection with any tissue protection sleeve disclosed herein. As illustrated, the outer sleeve 205A includes a central longitudinal axis 1117. In addition, as illustrated, the outer sleeve 205A includes two pin channels 1115 but other embodiments may have any number of pin channels including, for example, one, three, four, or more. In the depicted embodiment, the pin channels 1115 are located on an outer surface of the outer sleeve 205A and extend substantially the entire longitudinal length of the outer sleeve 205A. However, in some embodiments, the pin channels 1115 may extend along only a portion of the longitudinal length of the outer sleeve 205A. As illustrated, the pin channels 1115 may be non-parallel to the central longitudinal axis 1117 of the outer sleeve 205A but in some embodiments the pin channels 1115 may be parallel to the central longitudinal axis 1117. In use, each of the pin channels 1115 are arranged and configured to receive a pin 112 (best seen in FIG. 19) to couple the tissue protection sleeve to a patient's bone. In addition, the outer sleeve 205A may include a hole 1113. As previously mentioned, the hole 1113 may extend generally transverse to the longitudinal axis 1117. In use, the hole 1113 may be used to couple a tissue protection sleeve handle 125 to the outer sleeve 205A.

Figure 18:
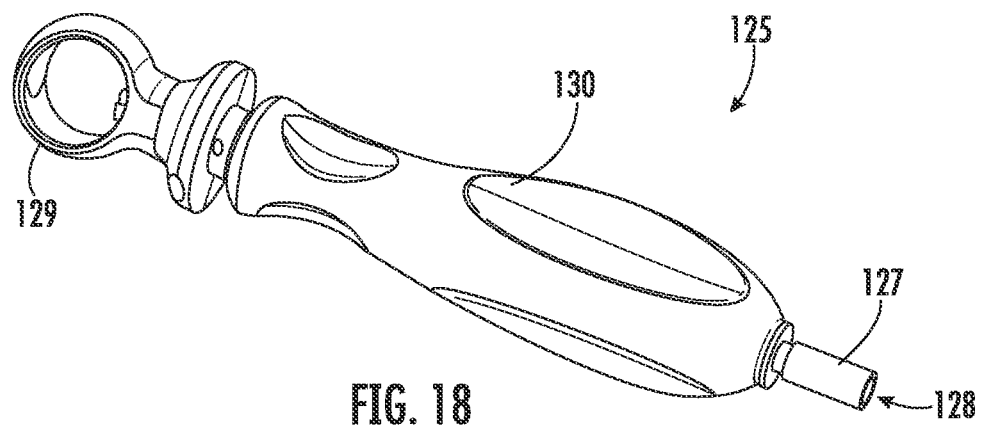
FIG. 18 illustrates an embodiment of a tissue protection sleeve handle arranged and configured to be used with the various embodiments of the present disclosure.
Figure 19:
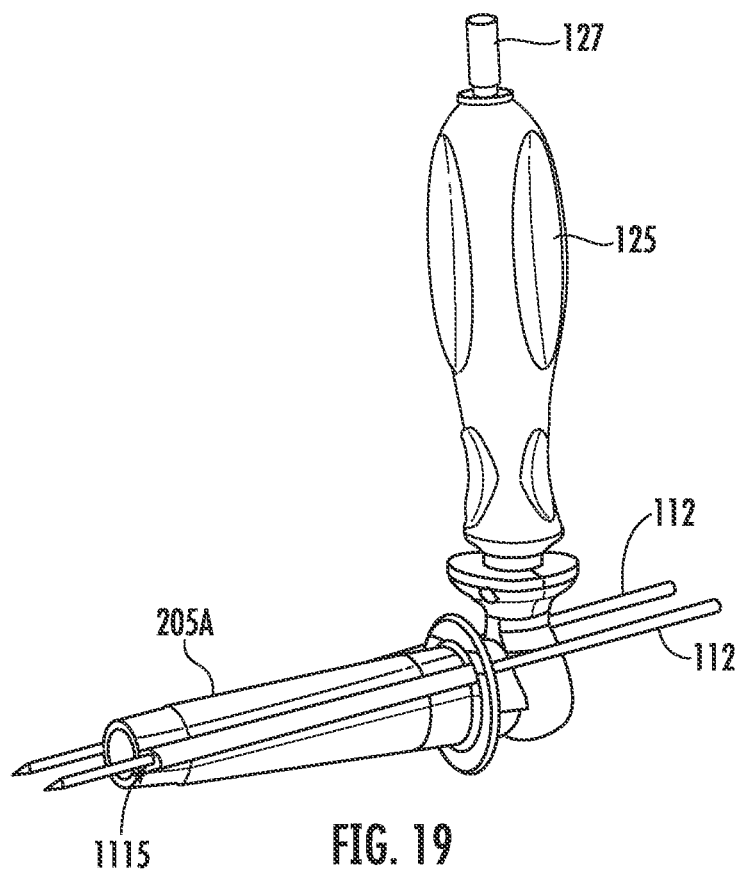
FIG. 19 illustrates a perspective view of a tissue protection sleeve handle coupled with the second embodiment of the outer sleeve.

Referring to FIG. 18, an embodiment of a tissue protection sleeve handle 125 in accordance with one or more features of the present disclosure is illustrated. In use, the tissue protection sleeve handle 125 may be used with any of the tissue protection sleeves of the current disclosure. As illustrated, the tissue protection sleeve handle 125 includes a gripping portion 130 arranged and configured to be grasped or held by a user to hold on to the tissue protection sleeve handle 125, and thus, the tissue protection sleeve. In addition, the tissue protection sleeve handle 125 may include a locking mechanism such as, for example, a spring mounted plunger 127 arranged and configured to be inserted into a hole such as, for example, hole 1113 (FIG. 16) formed in the outer sleeve 205A to ensure proper orientation as will be described in greater detail below. The tissue protection sleeve handle 125 may also include a ring 129, which, as an example, may be used to grip or couple to a tissue protection sleeve such as, for example, tissue protection sleeve 205A. The assembled tissue protection sleeve and guide handle construct is shown in FIG. 19, which also illustrates the use of pin channels 1115, which as illustrated, each receive a pin 112 to couple the outer sleeve 205A and thus the tissue protection sleeve to a patient's bone. In use, the outer sleeve 205A may be placed proximate to the end of a patient's long bone, and bone pins 112 can be inserted through the pin channels 1115 and into the bone, securing the tissue protection sleeve to the patient.

Figure 20:
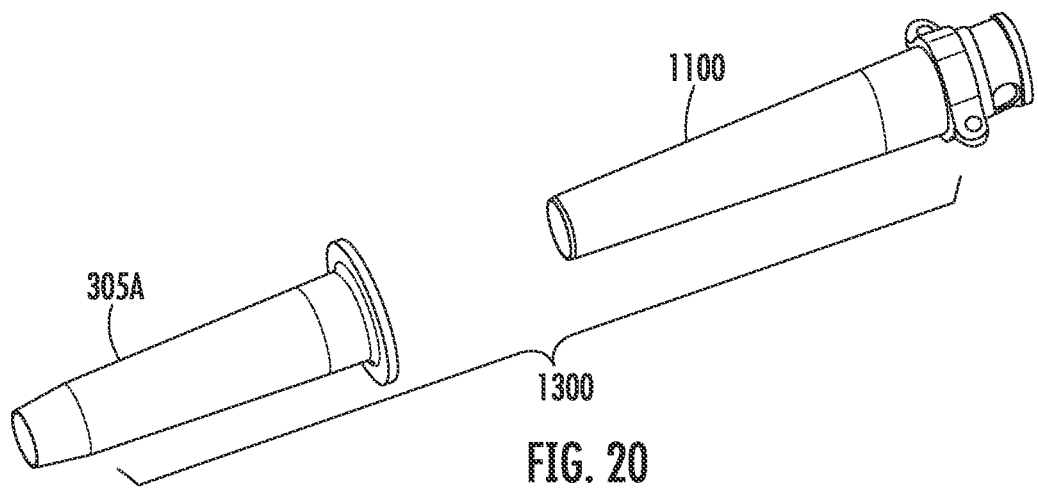
FIG. 20 illustrates an exploded view of an eighth embodiment of an inner sleeve and a third embodiment of an outer sleeve.
Figure 21:
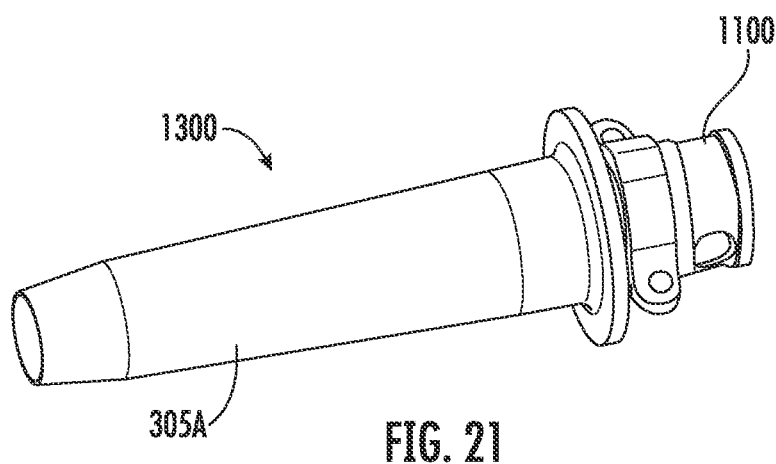
FIG. 21 illustrates a perspective view of the third embodiment of the outer sleeve coupled with the eleventh embodiment of the inner sleeve.
Figure 22:
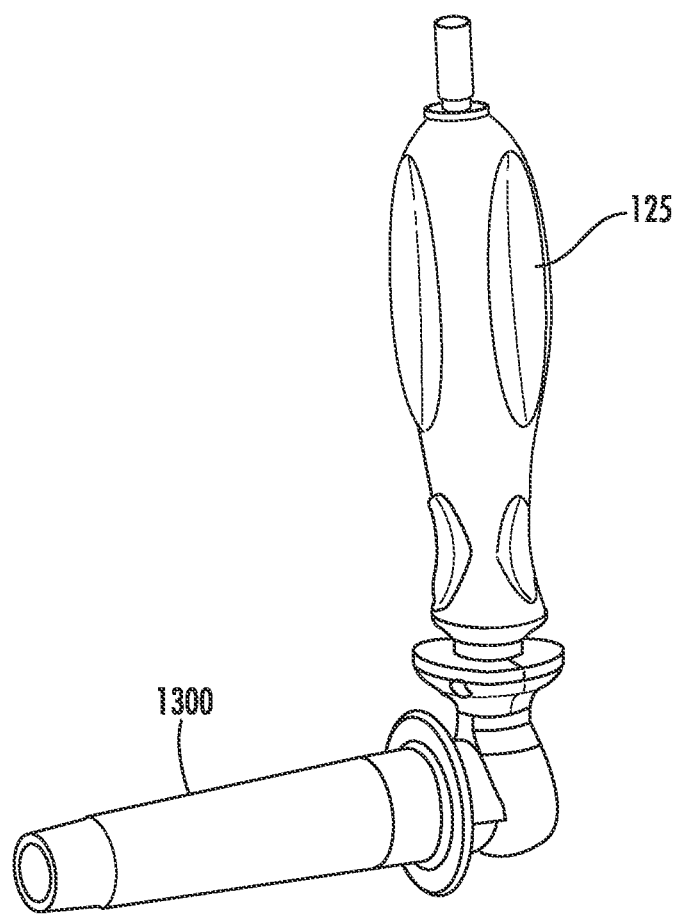
FIG. 22 illustrates a perspective view of a tissue protection sleeve handle coupled with the tissue protection sleeve shown in FIG. 21.

Referring to FIGS. 20-22, another embodiment of a tissue protection sleeve in accordance with one or more features of the present disclosure is illustrated. As illustrated, an inner sleeve 1100 is inserted into (e.g., placed inside of) an outer sleeve 305A to make tissue protection sleeve or construct 1300. As illustrated, an alternate embodiment of an inner sleeve 1100 is illustrated, although the inner sleeve may be any other inner sleeve described herein. Similarly, as illustrated, a third embodiment of an outer sleeve 305A is illustrated, although the outer sleeve may be any other outer sleeve described herein. For example, in the illustrated embodiment, the outer sleeve 305A may be made from a flexible rubber material. Alternatively, the outer sleeve 305A may be made of a soft polymer to protect a patient's soft tissues. In various embodiments, the outer sleeve 305A may be arranged and configured to be squeezed, squished, flatten, or the like. In use, the outer sleeve 305A acts as a thin cushion between the backside of a patient's bone and the inner sleeve 1100. In various embodiments, the outer sleeve 305A may also include one or more air pockets or channels located longitudinally or radially within a thickness of the outer sleeve 305A. For example, in one embodiment, the outer sleeve 305A may include a plurality of grooves spaced longitudinally in the outer surface of the outer sleeve 305A. Thus arranged, the grooves provide stress relief during insertion of the tissue protection sleeve into the patient's bone. As previously mentioned, in use, a tissue protection sleeve handle such as, for example, tissue protection sleeve handle 125 may be coupled with the assembled construct 1300 as illustrated in FIG. 22.

Figure 23:
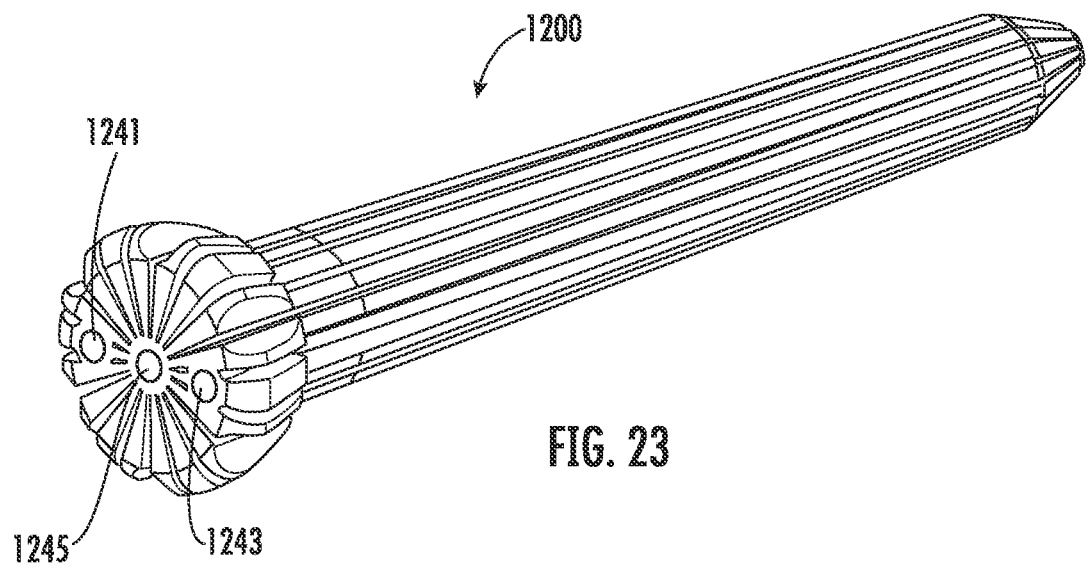
FIG. 23 illustrates a perspective view of an embodiment of a pin sleeve in accordance with one or more features of the present disclosure.
Figure 24:
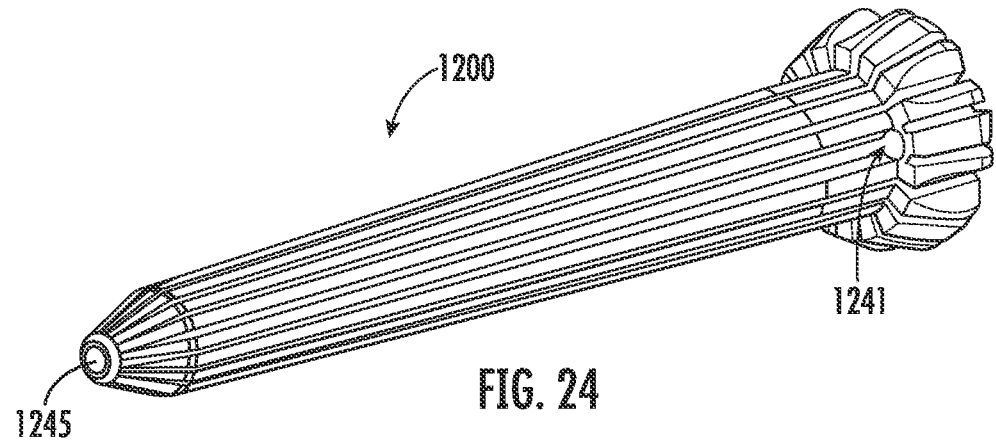
FIG. 24 illustrates an additional perspective view of the pin sleeve shown in FIG. 23.

FIGS. 23-35 illustrate another embodiment of the present disclosure and a surgical method for placing a tissue protection sleeve on a patient's bone. Referring to FIGS. 23 and 24, an embodiment of a pin sleeve 1200 is illustrated. As will be described herein, in use, the pin sleeve 1200 may be used in place of the inner sleeves described herein. In use, the pin sleeve 1200 is arranged and configured to enable the tissue protection sleeve to be coupled or fixed to a patient's bone and to guide, for example, a reamer during a surgery. That is, as will be described herein, in use, the pin sleeve 1200 facilitates insertion of a centrally located pin, which may be used to guide a reamer to form the intramedullary canal in the patient's bone.

The pin sleeve 1200 may be manufactured from any suitable material now known or hereafter developed. For example, in various embodiments, the pin sleeve 1200 may be made of an injection molded plastic. Alternatively, the pin sleeve 1200 may be made of a metal. In either event, as illustrated, the pin sleeve 1200 includes a plurality of peripheral pin channels or pin locator holes 1241, 1243, although it is envisioned that the pin sleeve 1200 may include more or less pin locator holes. In use, in the illustrated embodiment, the pin locator holes 1241, 1243 extend through the length of the pin sleeve 1200. In addition, with continued reference to FIGS. 23 and 24, the pin sleeve 1200 may include a third, centrally located pin channel or pin locator hole 1245. In use, the pin sleeve 1200 may be inserted into (e.g., placed inside) any of the outer sleeves of the current disclosure. A particular advantage of the embodiments shown in FIGS. 23-35 is that surgical access is often limited in the region behind a patient's patella, and it is desirable to make any instruments as compact as possible. By shifting placement of the pins 112 from the outside of the outer sleeve to the pin sleeve 1200, the outer dimensions of the outer sleeve may be reduced.

Figure 25:
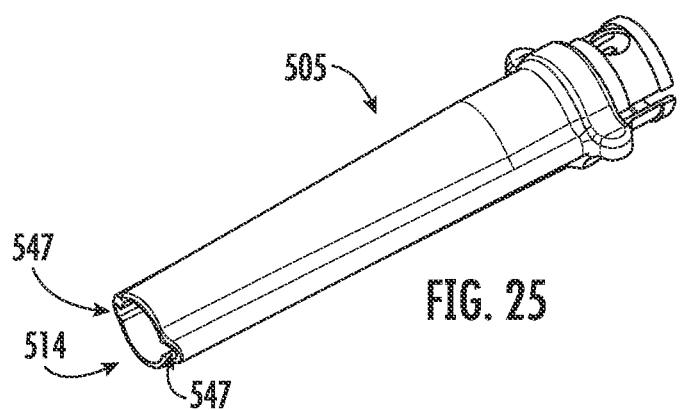
FIG. 25 illustrates a perspective view of a fourth embodiment of an outer sleeve in accordance with one or more features of the present disclosure.
Figure 26:
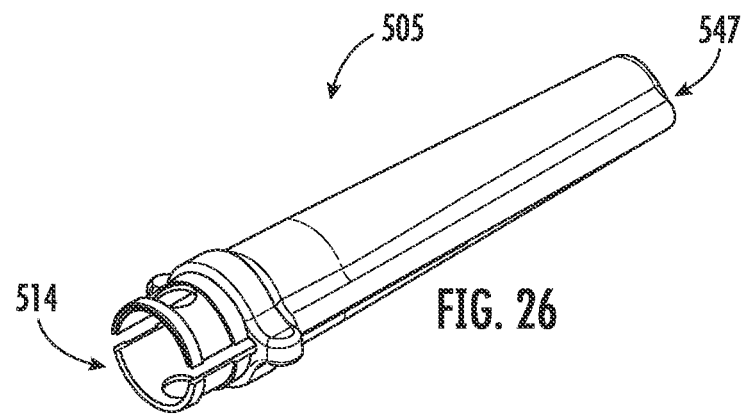
FIG. 26 illustrates an additional perspective view of the outer sleeve shown in FIG. 25.

Referring to FIGS. 25 and 26, an alternate embodiment of an outer sleeve 505 is illustrated. In use, the outer sleeve 505 may be used in connection with any tissue protection sleeve disclosed herein. As illustrated, the outer sleeve 505 is substantially similar to the outer sleeve 205A shown and described in connection with FIGS. 16 and 17 except for the pin channels 547 being opened to an interior bore 514 of outer sleeve 505 for reasons that will become apparent below.

Figure 27:
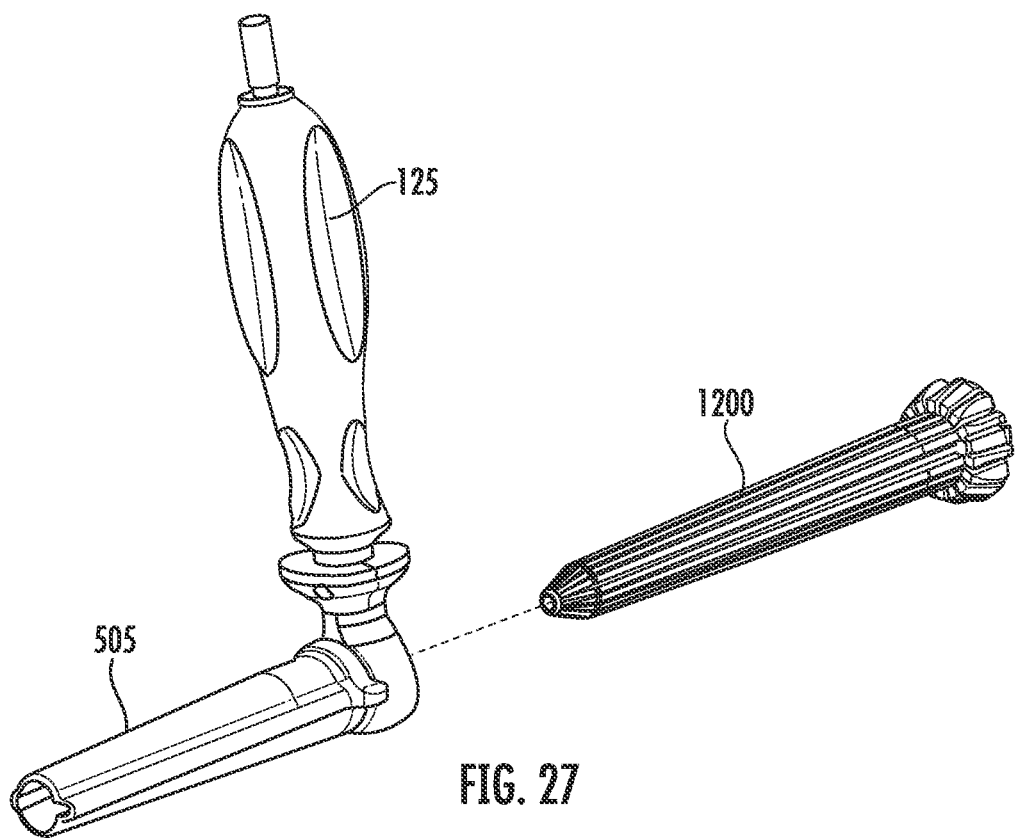
FIG. 27 illustrates a perspective view of the outer sleeve shown in FIG. coupled with a tissue protection sleeve handle.
Figure 28:
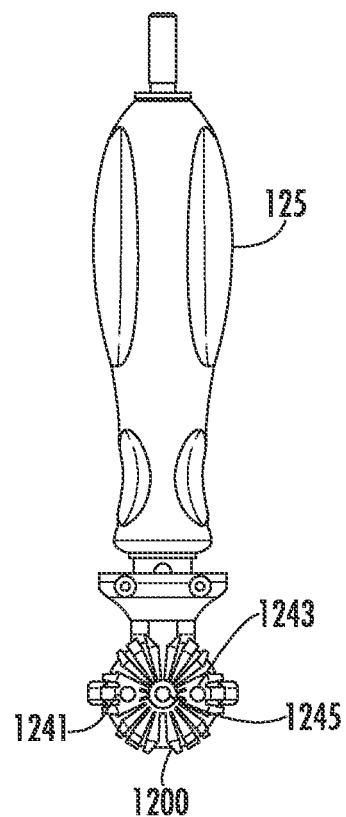
FIG. 28 illustrates an end view of the tissue protection sleeve handle coupled with a pin sleeve and the fourth embodiment of the outer sleeve.
Figure 29:
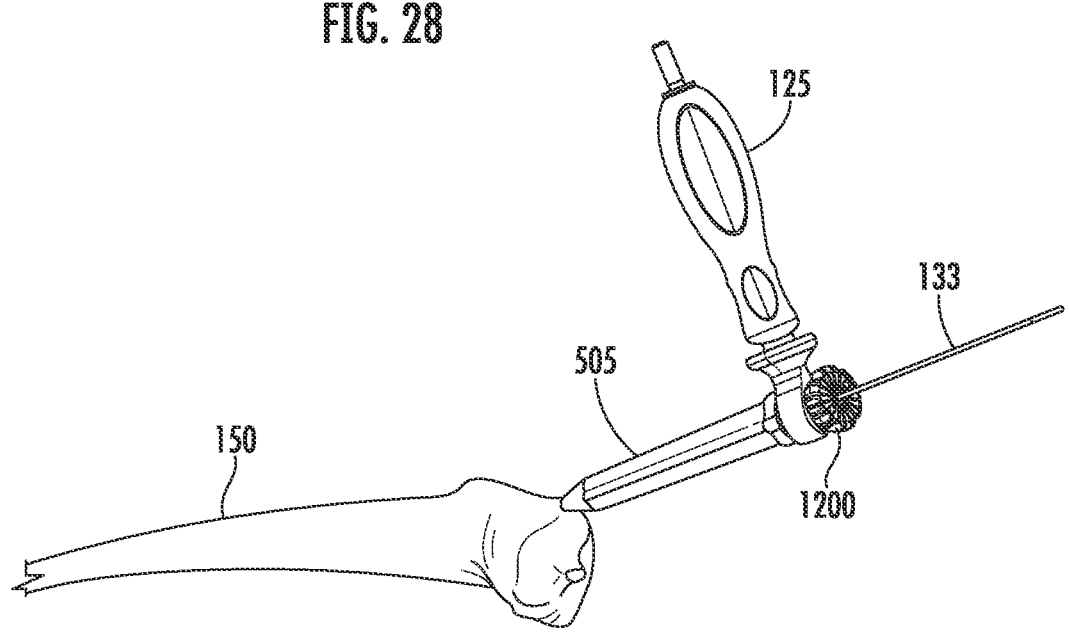
FIG. 29 illustrates a perspective view of the fourth embodiment of the outer sleeve coupled with a tissue protection sleeve handle approaching a patient's bone.
Figure 30:
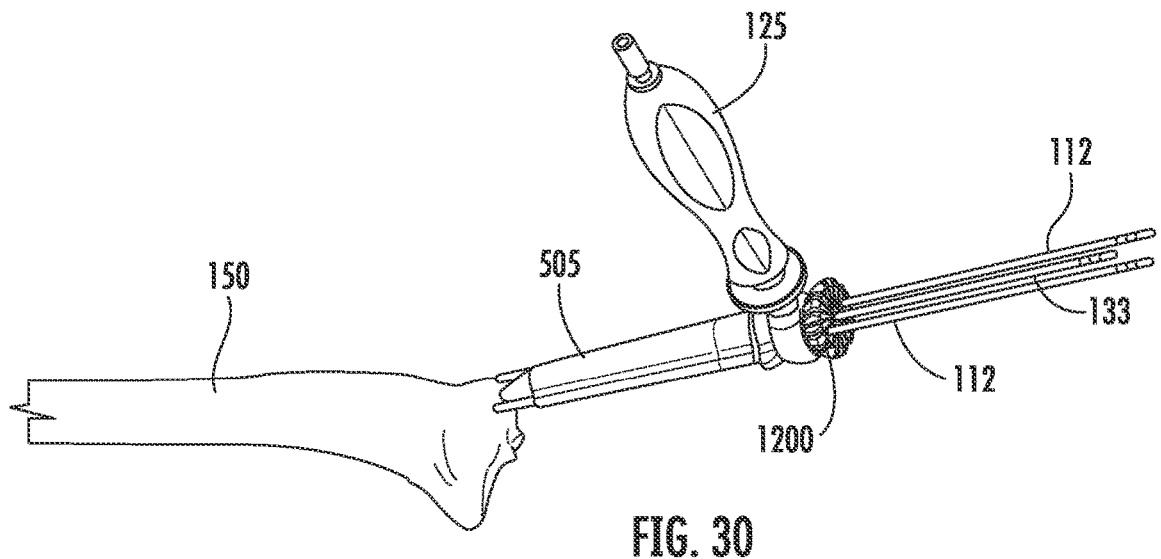
FIG. 30 illustrates a perspective view of the fourth embodiment of the outer sleeve coupled with the tissue protection sleeve handle and pinned to a patient's bone.

With reference to FIGS. 27-35, an embodiment of a surgical method or sequence that may be employed in accordance with one or more features of the present disclosure will now be described. In use, a pin sleeve such as, for example, pin sleeve 1200 may be initially inserted into an outer sleeve such as, for example, outer sleeve 505. In one embodiment, the outer sleeve 505 may already be engaged with the tissue protection sleeve handle 125 as shown in FIG. 27. Next, a user ensures that the locking mechanism such as, for example, a spring mounted plunger 127, of the tissue protection sleeve handle 125 fixes the pin sleeve 1200 in the proper orientation with respect to the outer sleeve 505. This is done by making sure that the pin channels 547 formed on the outer sleeve 505 are aligned with the pin channels 1241, 1243 formed on the pin sleeve 1200. This may be done visually by looking at the end of the pin sleeve 1200, as shown in FIG. 28. Next, as shown in FIG. 29, a user manipulates the tip of the pin sleeve 1200 into proper orientation with a patient's bone 150. Once properly positioned, the surgeon may drill and position a central guide pin 133 through the centrally located pin locator hole 1245 of the pin sleeve 1200. Next, as shown in FIG. 30, additional pins 112 may be inserted into pin channels 1241, 1243 of the pin sleeve 1200 and drilled into the patient's bone 150. In one embodiment, the spring mounted plunger 127 may include an internal borehole 128 (FIG. 18) to enable suctioning.

Figure 31:
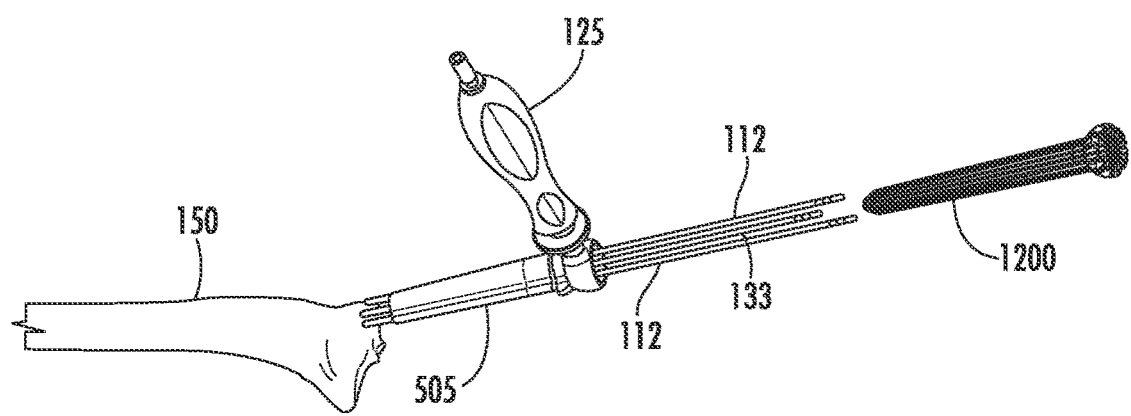
FIGS. 31-35 illustrate perspective views of a surgical method in which the fourth embodiment of the outer sleeve and a pin sleeve are used to pin the outer sleeve to a patient's bone.
Figure 32:
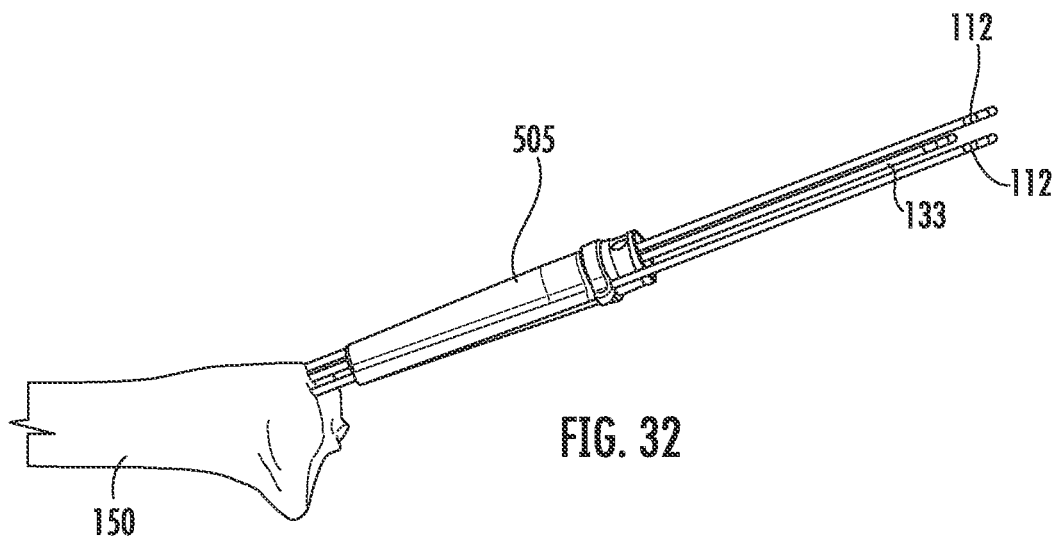
Figure 33:
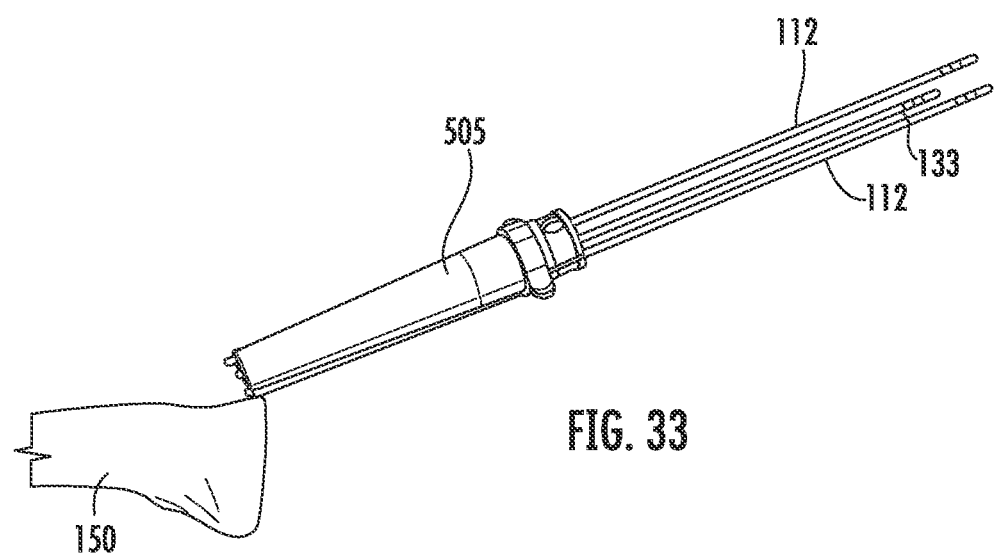
Figure 34:
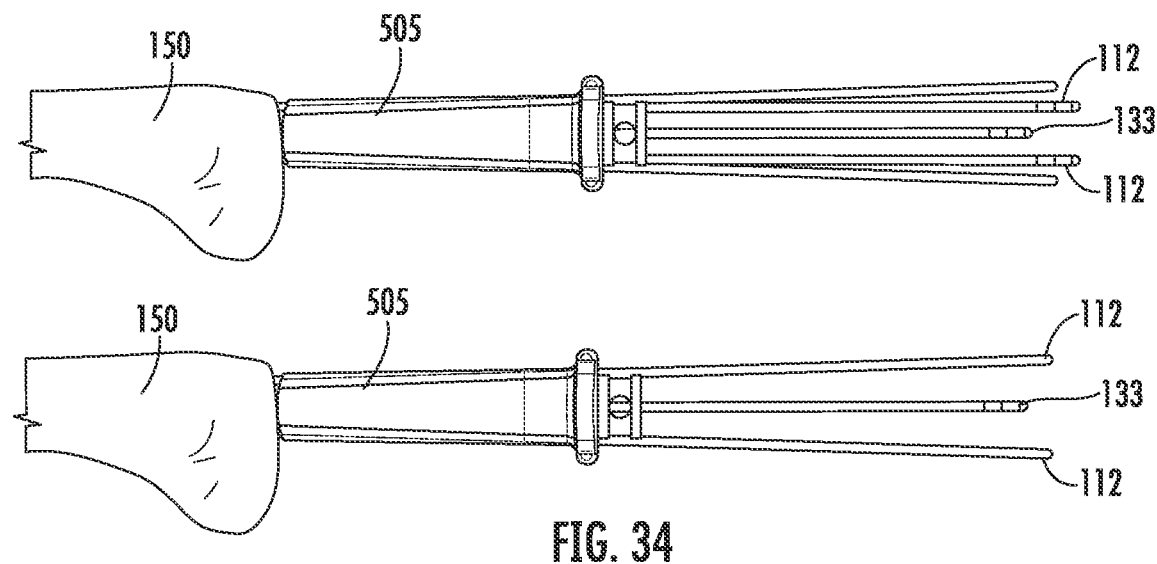
Figure 35:
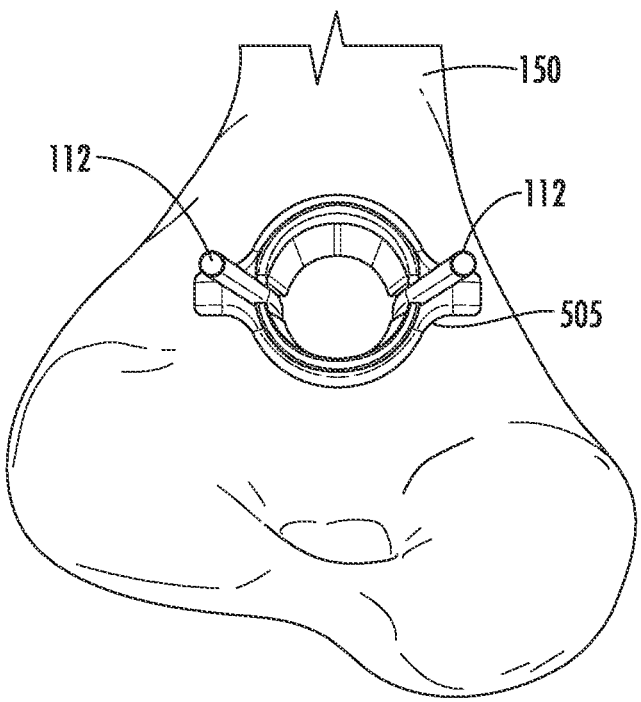

With reference to FIGS. 31 and 32, the pin sleeve 1200 may now be removed from the outer sleeve 505 and discarded. In addition, the tissue protection sleeve handle 125 may be removed as well. Next, as shown in FIG. 33, the outer sleeve 505 may be pushed down adjacent to or in contact with the patient's bone 150. Finally, with reference to FIG. 34, the pins 112 may be bent or moved outwards into pin channels 547 until they snap into place. That is, as best seen in FIG. 25, pin channels 547 are open to the inner bore 514 of the outer sleeve 505, but the opening between the inner bore 514 and the pin channels 547 may be slightly less than the diameter of pins 112 (e.g., the pin channels 547 include an opening, the opening being in communication with the inner bore 514 formed in the tissue protection sleeve so that a pin 112 can be moved between the bore and the opening). Finally, a reamer (not shown) can be advanced over the central pin 133 and the intramedullary canal of the patient's bone 150 may be reamed. An end view of outer sleeve 505 positioned on bone 150 is shown in FIG. 35. As an alternative, or additionally, an object may be pushed into the bore of the outer sleeve 505 after the pin sleeve 1200 has been removed, to urge the pins 112 into pin channels 547.

Figure 36:
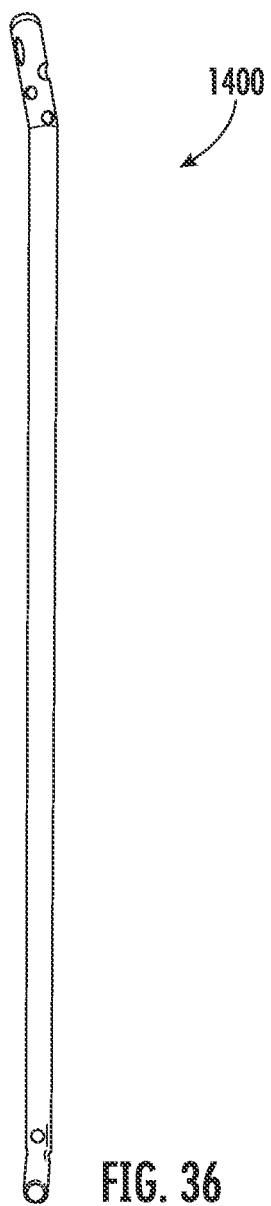
FIG. 36 illustrates a perspective view of an embodiment of an intramedullary nail that may be inserted into a patient's bone using the tissue protection sleeve.

With reference to FIG. 36, an embodiment of an IM nail 1400 is disclosed, although this is but one configuration and any other now known or hereafter developed IM nail may be used. In use, the IM nail 1400 may be provided in a kit with one or more tissue protection sleeves and/or components thereof as described herein. In use, the tissue protection sleeves of the present disclosure are arranged and configured to provide a pathway for inserting the IM nail into a patient's bone such as, for example, inserting the IM nail into a patient's proximal tibial while protecting the patient's patellar structures and other soft tissues during insertion.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Any embodiment or feature of any section, portion, or any other component shown or particularly described in relation to various embodiments of similar sections, portions, or components herein may be interchangeably applied to any other similar embodiment or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. A tissue protection sleeve arranged and configured to facilitate insertion of an intramedullary ("IM") nail into a patient's bone, the tissue protection sleeve comprising:
an inner sleeve including a first end portion, a second end portion, a longitudinal axis, and a bore extending there through from the first end portion to the second end portion; and
a flexible outer sleeve including a first end portion, a second end portion, a cannulated inner bore extending from the first end portion to the second end portion of the flexible outer sleeve, and an outer surface, the cannulated inner bore of the flexible outer sleeve being arranged and configured to at least partially receive and surround the inner sleeve, the flexible outer sleeve further including first and second pin channels formed on the flexible outer surface of the outer sleeve so that at least a portion of the first and second pin channels protrude from the outer surface, the first and second pin channels extending along a portion of an entire longitudinal length of the flexible outer sleeve;
wherein the tissue protection sleeve is capable of bending without collapsing, in part or in total, the bore; and
wherein the pin channels are angled about the flexible outer surface of the outer sleeve as the pin channels extend from the first end portion to the second end portion of the flexible outer sleeve such that the pins channels extend non-parallel and circumscribe a portion of the outer surface of the flexible outer sleeve.

2. The tissue protection sleeve of claim 1, wherein the flexible outer sleeve comprises a polymer.

3. The tissue protection sleeve of claim 1, wherein the flexible outer sleeve comprises silicone rubber.

4. The tissue protection sleeve of claim 1, wherein the inner sleeve comprises a plurality of independent and separate segments arranged along the longitudinal axis from the first end portion to the second end portion.

5. The tissue protection sleeve of claim 4, wherein one or more of the plurality of segments include a projection extending away from a proximal side thereof towards a distal side of an adjacent segment.

6. The tissue protection sleeve of claim 1, wherein the inner sleeve comprises a unitary member including one or more cuts formed therein so that the inner sleeve can flex about the longitudinal axis.

7. The tissue protection sleeve of claim 6, wherein the one or more cuts comprise a spiral groove formed in the inner sleeve.

8. The tissue protection sleeve of claim 6, wherein the one or more cuts comprise one of an interrupted spiral cut pattern, a bespoke cut pattern, or a radial cut pattern.

9. The tissue protection sleeve of claim 1, wherein the bore of the inner sleeve comprises a tapered bore having a smaller cross-sectional area adjacent to the second end portion and a larger cross-sectional area adjacent to the first end portion.

10. The tissue protection sleeve of claim 1, further comprising a handle coupled to the first end portion of the flexible outer sleeve.

11. The tissue protection sleeve of claim 1, wherein the first and second pin channels extend substantially the entire longitudinal length of the flexible outer sleeve.

* * * * *